United States Patent
Spaulding

Patent Number: 5,906,627
Date of Patent: May 25, 1999

[54] CATHETER DEVICE HAVING A SELECTIVELY FLEXIBLE HOUSING

[76] Inventor: Ronald Nicholas Spaulding, 2261 McLaughlin Ave., Apt. 1, San Jose, Calif. 95122

[21] Appl. No.: 08/890,787

[22] Filed: Jul. 11, 1997

Related U.S. Application Data

[62] Division of application No. 08/610,578, Mar. 7, 1996.

[51] Int. Cl.$^6$ ............................................. A61B 17/22
[52] U.S. Cl. ............................ 606/159; 606/167; 604/22
[58] Field of Search ................................. 606/159, 167, 606/170, 171, 180, 22, 96; 128/750–755

[56] References Cited

U.S. PATENT DOCUMENTS

| | | |
|---|---|---|
| 4,587,972 | 5/1986 | Morantte, Jr. . |
| 4,637,401 | 1/1987 | Johnston . |
| 4,674,336 | 6/1987 | Johnston . |
| 4,781,186 | 11/1988 | Simpson et al. . |
| 4,802,490 | 2/1989 | Johnston . |
| 4,979,951 | 12/1990 | Simpson . |
| 5,024,234 | 6/1991 | Leary et al. . |
| 5,226,909 | 7/1993 | Evans et al. . |
| 5,269,793 | 12/1993 | Simpson . |
| 5,312,425 | 5/1994 | Evans et al. . |
| 5,403,334 | 4/1995 | Evans et al. . |
| 5,514,115 | 5/1996 | Frantzen et al. . |
| 5,624,457 | 4/1997 | Farley et al. . |

*Primary Examiner*—Michael Buiz
*Assistant Examiner*—Daphna Shai

[57] ABSTRACT

Disclosed herein is a catheter device which is operably positionable for use in a biological conduit. The catheter device includes a catheter body having a proximal end and a distal end; a flexible housing; a work element and a sleeve. The housing connects to the distal end of the catheter body and holds the work element. The sleeve slidably mounts with housing for selectively reinforcing the housing to inhibit bending. Accordingly, the housing is normally flexible to facilitate insertion of the catheter device into a biological conduit. When the sleeve moves with respect to the housing, the sleeve reinforces the housing to facilitate operation of the work element.

6 Claims, 7 Drawing Sheets

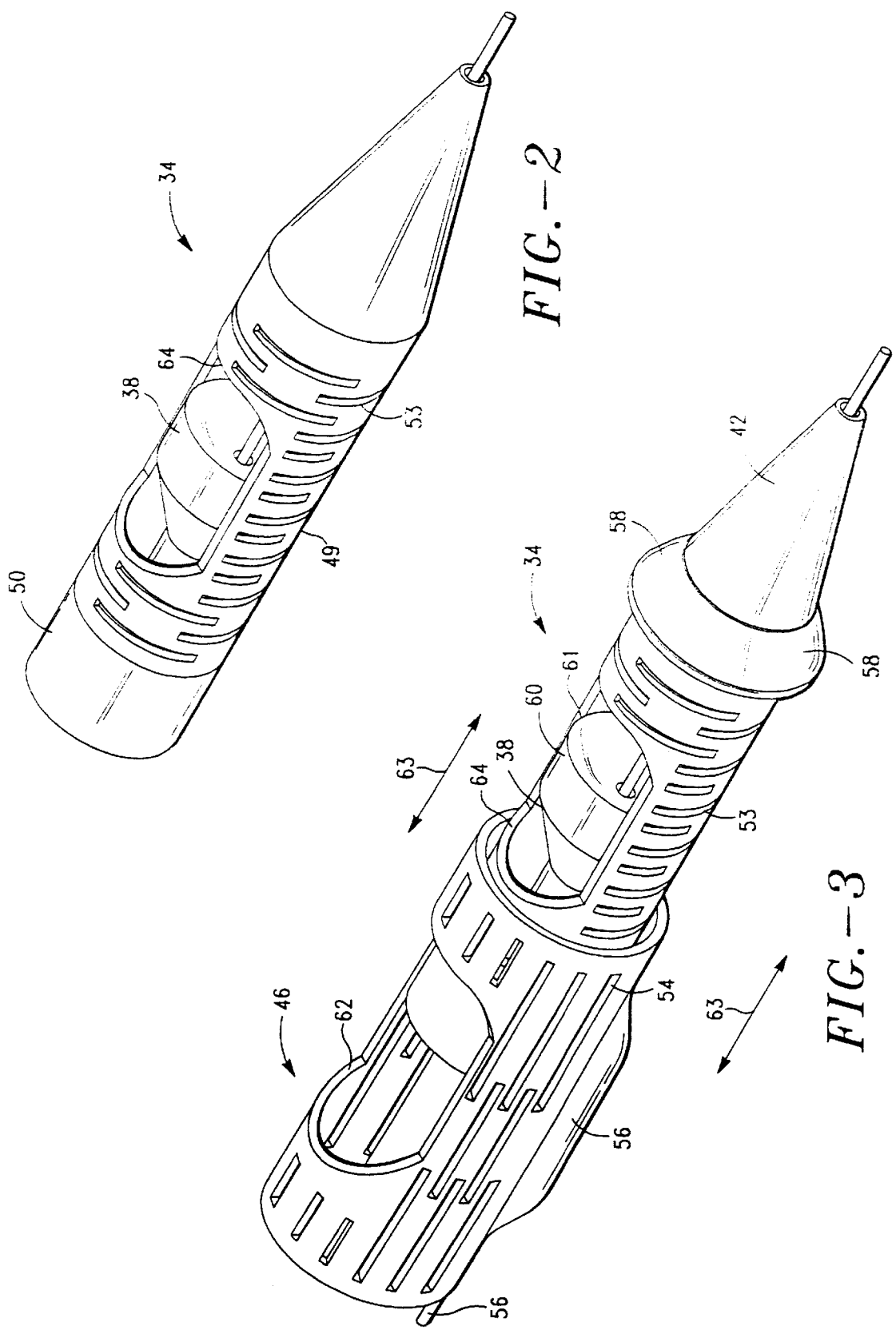

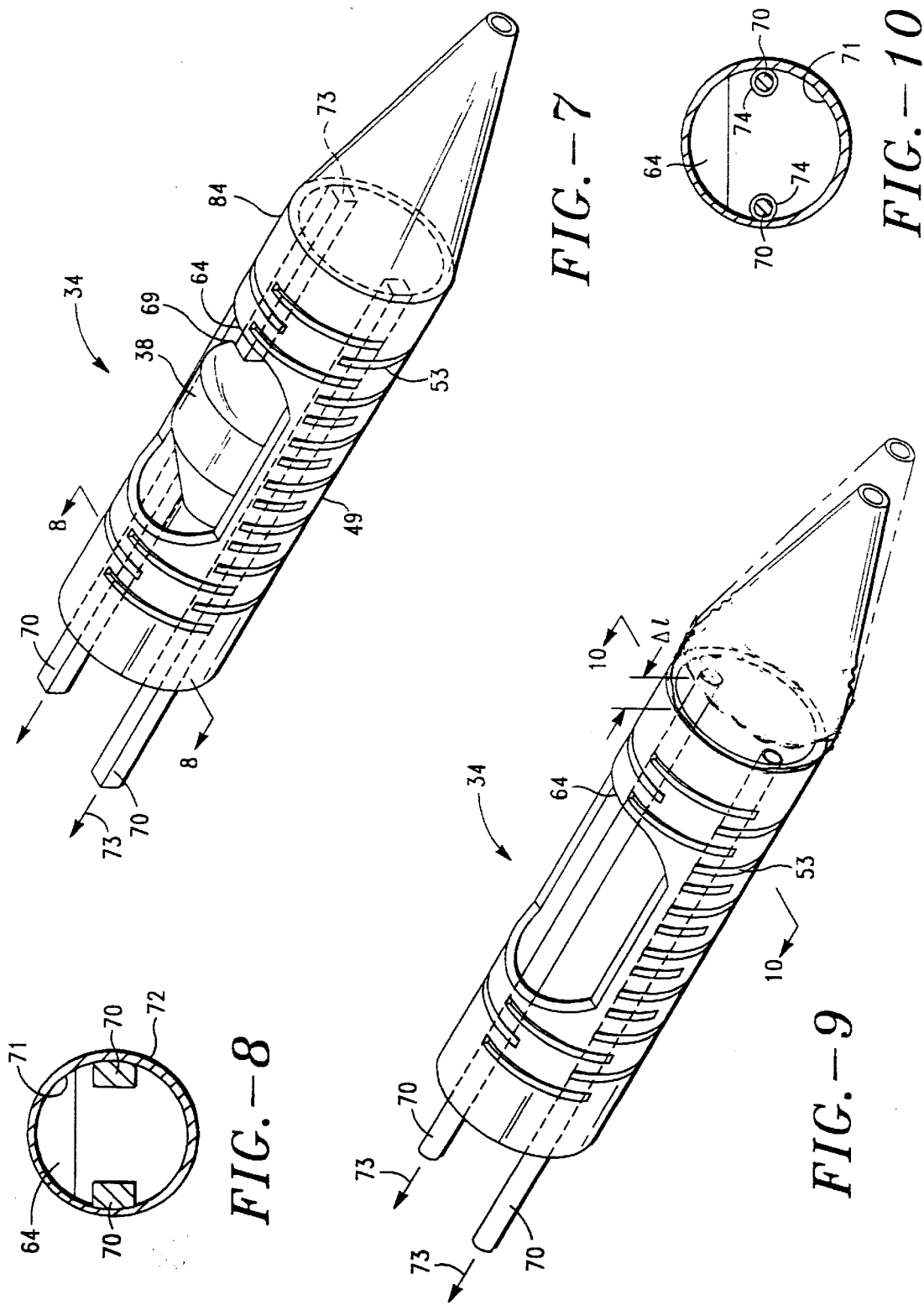

CATHETER DEVICE HAVING A SELECTIVELY FLEXIBLE HOUSING

This is divisional of copending application Ser. No. 08/610,578 filed on Mar. 7, 1996.

RELATED PATENTS AND PATENT APPLICATIONS

This invention relates in subject matter to commonly assigned U.S. patent application Ser. No. 08/357,999, filed Dec. 16, 1994, entitled "INTRAVASCULAR STRUCTURE WITH GUIDING STRUCTURE" to Hundertmark, et al., and U.S. Pat. No. 5,624,457, issue date Apr. 29, 1997, entitled "DIRECTIONAL ATHERECTOMY DEVICE WITH FLEXIBLE CUTTER" to Farley et al. and U.S. Pat. Nos. 4,781,186 and 5,312,425. The disclosure of each related patent and patent application is incorporated herein by reference.

BACKGROUND OF THE INVENTION

1. Field of the Invention

This invention relates to catheters which are insertable into a biological conduit such as a blood vessel. More particularly, this invention relates to atherectomy catheters having flexible housings.

2. Previous Art

Atherosclerosis is a disease characterized by the presence of biological-tissue such as atheroma, plaque and other material, on the interior walls of blood vessels. Such biological tissue is generally known as stenotic material. Stenotic material typically includes soft tractable material, or hardened material such as calcification. Stenotic material may be deposited throughout the vasculature and is commonly found in peripheral blood vessels that feed the arms and leas and in coronary blood vessels that feed the heart. Stenotic material may accumulate in localized regions, occluding the blood vessel and restricting blood flow. Restricted blood flow, in the coronary artery for example, can cause severe health problems including heart attacks and strokes.

Numerous ways of restoring blood flow have been proposed. Balloon angioplasty, for example, uses a balloon-tipped catheter to dilate the occluded region of the blood vessel. Laser angioplasty uses a laser to direct energy to ablate atheroma portions. Atherectomy uses a catheter having a cutter to sever and remove stenosis from an occluded portion of a blood vessel.

During an atherectomy procedure, a guidewire is first inserted into the vasculature of a patient via the femoral artery, for example. The guidewire advances through the vasculature to the stenosed region of an occluded blood vessel having a stenosed region. The catheter slides over, and along, the guidewire until the distal end of the atherectomy catheter positions adjacent the stenosis.

A typical atherectomy catheter has a work element such as a cutter and a housing with an opening. The housing attaches to the distal end of the atherectomy cutter and retains the cutter. The opening of the housing exposes the cutting blade During use, the opening invaginates stenotic material which extends from a blood vessel wall through the opening. The cutter reciprocally advances past the opening. Each time the cutter advances, the cutter severs a small portion of the stenotic material and removes the severed material from the blood vessel wall. The severed stenotic material is urged into a storage area of the catheter by the cutter. Various catheters have a nose cone which attaches to the distal end of the housing or storing severed stenotic material.

Typically, the cutter has an arcuate cutting blade. The cutting blade rotates (or rotationally oscillates) when the cutter advances to optimize severance and removal of the stenotic material.

Although such atherectomy catheters have enjoyed wide-spread success in both peripheral and coronary, applications, certain design limitations persist. The vasculature has tortuous regions with tight bends. Tortuous regions may be inaccessible by a catheter having a rigid housing. This inaccessibility limits the usefulness of catheters.

To facilitate insertion of atherectomy catheters into blood vessels having tight bends, catheters having flexible housings have been developed. Catheters with flexible housings are disclosed in U.S. Pat. Nos. 4,781,186, 5,226,909 and 5,312,425, the disclosures of which are incorporated herein by reference.

Flexible housings also have certain limitations. When flexed, a flexible cutter housing may interfere with the operation of an enclosed cutter. In particular, bending and flexing of a flexible housing may inhibit axial advancement of the cutter within the housing. This can also slow rotation of the cutter and limit cutting effectiveness. Interference between the housing and the cutter can dull the cutter and deform the housing.

Attempts to overcome the limitations associated with flexible catheters nave manifested themselves. An example of a catheter with a flexible housing that minimizes interference with the cutter is described in commonly assigned U.S. patent application Ser. No. 08,224,169 filed Apr. 7,1994 (Attorney Docket No. DEV11467), the disclosure of which is incorporated by reference above. The flexible cutter relies on a moveable saddle which attaches to the cutter. The saddle guides the cutter to avoid interference between the cutter and the housing.

Saddles and other guiding assemblies which are small enough to fit in the housing of an atherectomy catheter are difficult and expensive to manufacture. Guiding assemblies can limit flexion of an otherwise flexible housing. Improved intravascular catheters are desired which are easy to manufacture. It is also desirable to have a catheter with a flexible housing which does not require an added guiding assembly to guide and direct the cutter. It is also desirable to provide a way of retaining the work element in the catheter housing which is compatible with flexible housings cl various sizes and configurations. It is also desirable to provide a catheter having a flexible housing which is useful for removing stenotic deposits from blood vessels having tight bends.

SUMMARY AND OBJECTS OF THE INVENTION

The various objects of the invention which are presented and which will become apparent below are provided by example only and are not intended to limit the scope of the present invention. The present invention is to be limited in scope only by the appended claims.

It is an object of this invention to provide an intravascular catheter having a flexible housing which selectively flexes to enable insertion of the catheter into tortuous regions of blood vessels.

It is an object of this invention to provide a catheter having a flexible housing which is capable of becoming rigid to guide an axially moveable work element.

In accordance with the above objects and those that will be mentioned and will become apparent below, a catheter device for use in a biological conduit having torturous regions, comprises:

a catheter body having a proximal end and a distal end;

a housing connected to the distal end of the catheter body, the housing being flexible to facilitate insertion of the catheter device into the tortuous regions of the biological conduit, the housing being capable of guiding a moveable work element;

a work element moveable attached to operate within the housing; and a reinforcing means attached for selectively reinforcing the housing to facilitate operation of the work element, whereby, when the catheter device is inserted in the biological conduit, the reinforcing means selectively reinforces the housing to facilitate operation of the work element.

In a preferred embodiment, the work element is a rotatable cutter which axially reciprocates within the housing a The reinforcing means slides to inhibit flexion of the housing to minimize interference between the work element and the housing.

In another preferred embodiment, the reinforcing means includes a sleeve which slides from one position wherein the housing is flexible to another position wherein the sleeve circumscribes the housing. The sleeve provides external lateral support to the housing.

In another preferred embodiment, the housing has an opening for invaginating biological tissue when the catheter device inserts into a biological conduit. The reinforcing means slidably attaches to the housing to inhibit deformation of the opening during operation of the work element.

In another preferred embodiment, the reinforcing means includes a sleeve. The housing circumscribes a portion of the sleeve. The sleeve slides from one position wherein the housing is flexible to another position wherein the sleeve internally supports the housing to limit flexion of the housing.

In another preferred embodiment, the sleeve has an opening and the housing has an opening. The openings align when the sleeve internally supports the housing to enable the housing to invaginate biological tissue.

In another preferred embodiment, the housing is formed having a number of discrete segments. The reinforcing means includes a wire which attaches to the housing and extends along the housing. The wire is normally relaxed to facilitate flexion of the housing. The wire tenses to selectively reinforce the housing.

In another preferred embodiment, the housing is axially compressible to normally facilitate flexion of the housing. The reinforcing means includes a wire which is normally relaxed and extends along the housing. The wire slides and tenses to compress the housing. The wire tenses to selectively provide lateral support to the housing. The wire is enclosed in a protective covering.

It is an advantage of the present invention to provide a catheter having a selectively flexible housing.

It is a further advantage to provide a catheter having a selectively flexible housing which flexes to facilitate positioning of the catheter in a biological conduit and which selectively becomes rigid to facilitate operation of a moveable work element within the housing.

BRIEF DESCRIPTION OF THE DRAWINGS

FIG. 2 shows a perspective view of an embodiment of the housing of the catheter device of FIG. 1.

FIG. 3 shows a perspective view of the housing of FIG. 2 with a sleeve.

FIG. 7 shows a perspective view of an embodiment of a housing in accordance with the present invention.

FIG. 8 shows a cross-sectional view of an embodiment of the housing and the sleeve shown along the line 8—8 in FIG. 7 as seen in the direction of the arrows.

FIG. 9 shows a perspective view of an embodiment of the housing of FIG. 7.

FIG. 10 shows a cross-sectional view of the housing and the sleeve shown along the line 10—10 in FIG. 9 as seen in the direction of the arrows.

DETAILED DESCRIPTION OF THE INVENTION

Figure 1:
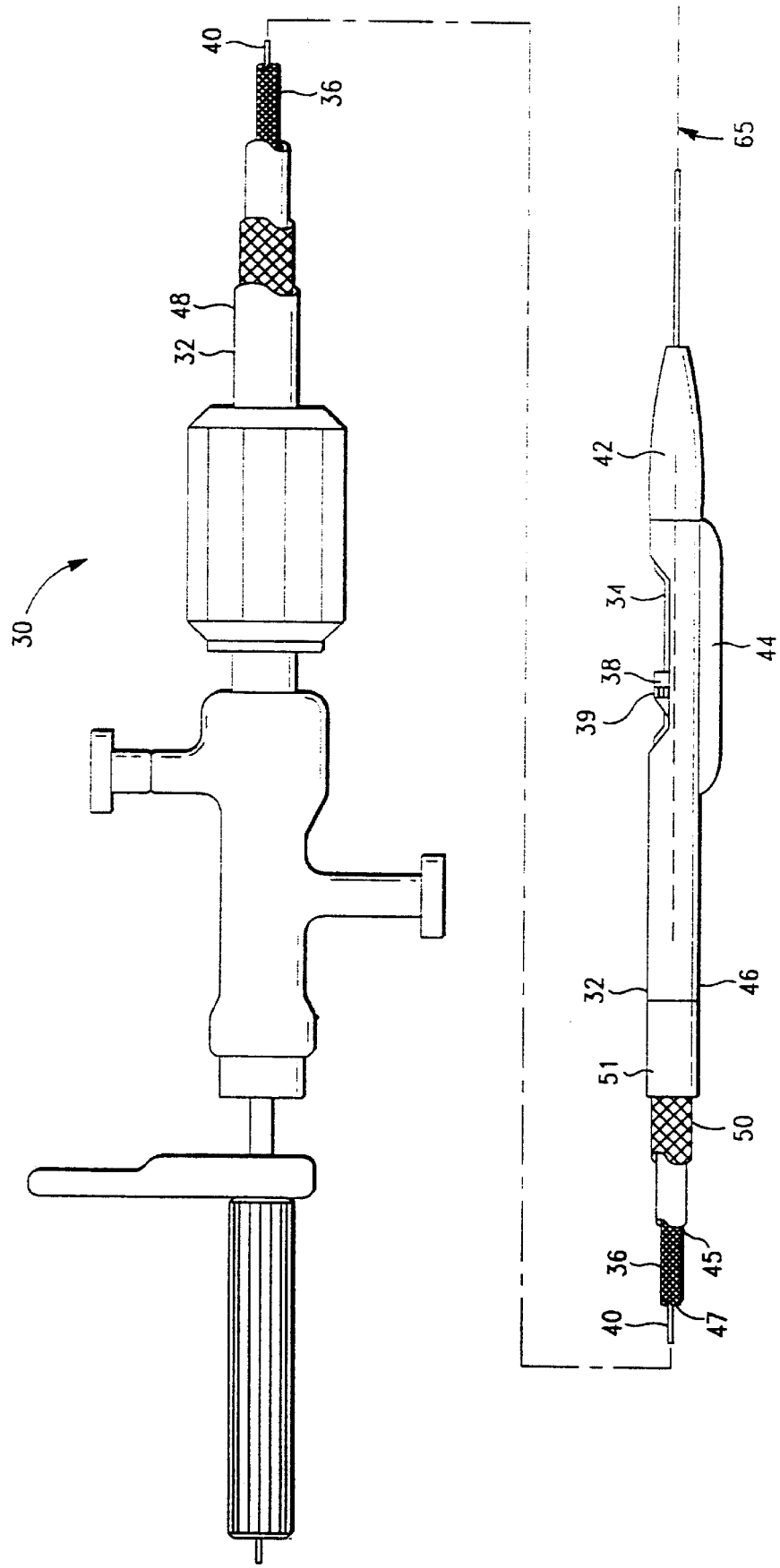
FIG. 1 shows an orthographic view of a catheter device in accordance with the present invention.

With particular reference to FIG. 1, there is shown a catheter device in accordance with the present invention. The catheter device is generally designated with the reference numeral 30. The catheter device 30 includes a catheter body 32, a housing 34, a torque cable 36, a work element 38, a sleeve 46, a nosecone 42 a balloon 44 and a guide wire 40.

The catheter body 32 has a proximal end 48 and a distal end 50. The catheter body 32 defines a cable lumen 45 that extends between the proximal end 48 and the distal end 50 and defines a catheter body axis. The housing 34 attaches to the distal end 50 of the catheter body 22. The nosecone 42 attaches to a distal end of the housing 34. The balloon 44 attaches to a lateral side of the housing 34.

The torque cable 36 extends through the cable lumen 45 and attaches to the work element 38 within the housing 34 to actuate the work element 38. The housing 34 has an axis 65. The torque cable 36 extends coaxially through the housing 34 to rotate and axially translate the work element 38.

The torque cable 36 defines a guide wire lumen 47. The guide wire 40 extends through the guide wire lumen 47, through the work element 38 and beyond the nosecone 42.

The housing 34 is flexible to enable the housing to bend when inserted into tortuous regions of a biological conduit such as an artery. The sleeve 46 slidably attaches to the housing 34 to selectively reinforce the housing 34. The sleeve 46 slides with respect to the housing 34 from a position where the housing 34 is flexible to another position where the sleeve 46 reinforces the housing 34. When the sleeve 46 reinforces the housing 34, the sleeve 46 laterally supports the housing 34 and thereby inhibits bending of the housing 34. Such lateral support facilitates retention of the work element 38 within the housing 3 by maintaining the housing 38 in an unflexed configuration.

The work element 38 Includes a sensor 39. The sensor 39 includes an ultrasonic sensor. It can be appreciated that a variety of sensors may be used with the work element in accordance with the present invention. It can be appreciated that a variety of work elements may be employed with the present invention. For example, a cutter and sensor can be simultaneously included with a single work element. U.S. U.S. Pat. No. 5,000,185 shows a catheter device having a sensor. The disclosure of this U.S. patent is incorporated herein by reference.

The nosecone 42 attaches to the distal end of the housing 34. The nosecone 42 is hollow to receive the guide wire 40 and guide the catheter device 30 over the guide wire 40. The nosecone 42 flexes laterally (bends) to guide the catheter device 30 through tortuous regions of a biological conduit. An example of a catheter device having a flexible nosecone is disclosed in U.S. Pat. No. 5,250,059, the disclosure of which is incorporated herein by reference.

The balloon 44 selectively inflates to urge the housing 34 into a desired position within a biological conduit. Catheter devices having balloons are disclosed in U.S. Pat. No. 5,092,873, Re. 33,569, and U.S. Pat. No. 5,071,425, the disclosures of which are incorporated herein by reference.

With particular reference to FIG. 2, there is generally shown the housing 34 of the present invention. The housing 34 attaches to the distal end 50 of the catheter body. The housing 34 has a surface 49. The surface 49 defines a plurality of radially aligned slots 53. The slots 53 radially align, each slot 53 circumscribing a portion of the housing 34. The slots 53 facilitate uniform flexibility of the housing 34. The slots 53 are sized and shaped having uniform length and width to facilitate a desired degree of torsional rigidity, lateral rigidity (bending strength) and axial strength of the housing 34. It can be appreciated that the distance between the slots, as well as the length, width and area of each slot, can be modified to vary the flexibility to the housing. An example of a flexible housing is disclosed in U.S. Pat. No. 4,781,186, the disclosure of which is incorporated herein by reference.

With particular reference to FIG. 3, the housing 34 and the sleeve 46 are generally shown. The sleeve 46 includes has an opening 62, a balloon 44 and a balloon inflation lumen 56. The sleeve 52 defines a plurality of axially aligned slots 54 which align axially with the sleeve 46. When the housing 34 bends and the sleeve 46 slides over the housing 34 to straighten the housing 34, the sleeve 46 maintains the housing 34 in a straightened (unflexed) configuration. The sleeve 46 minimizes flexion (e.g. bending) of the housing 34 by reinforcing the housing with a selected degree of rigidity.

The housing 34 defines an opening 64 which exposes the work element 38. The work element 38 includes a cutter 60. The cutter 60 has an arcuate cutting edge. The cutter 60 reciprocally advances in an axial direction within the housing 34 past the opening 64. The cutter 60 rotates during reciprocal advancement to cut biological tissue.

The nose cone 42 attaches to the distal end of the housing 34. A stopper 58 circumscribes the distal end of the housing 34 and a portion of the nosecone 42. The stopper 58 regulates advancement of the sleeve 46 with respect to the housing 34.

The sleeve 46 slides axially with respect to the housing 34 in the direction of the arrows 63. The sleeve 46 slides from one position (FIG. 3) where the opening 62 of the sleeve 46 is proximal to the opening 64 of the housing 34, to another position (FIG. 4) where the opening 62 of the sleeve 46 aligns with the opening 64 of the housing 34.

The stopper 58 is engageable with the sleeve 46 to hold the sleeve 46. Positioning the sleeve 46 wit, respect to the housing 34 regulates flexion of the housing 34.

Figure 4:
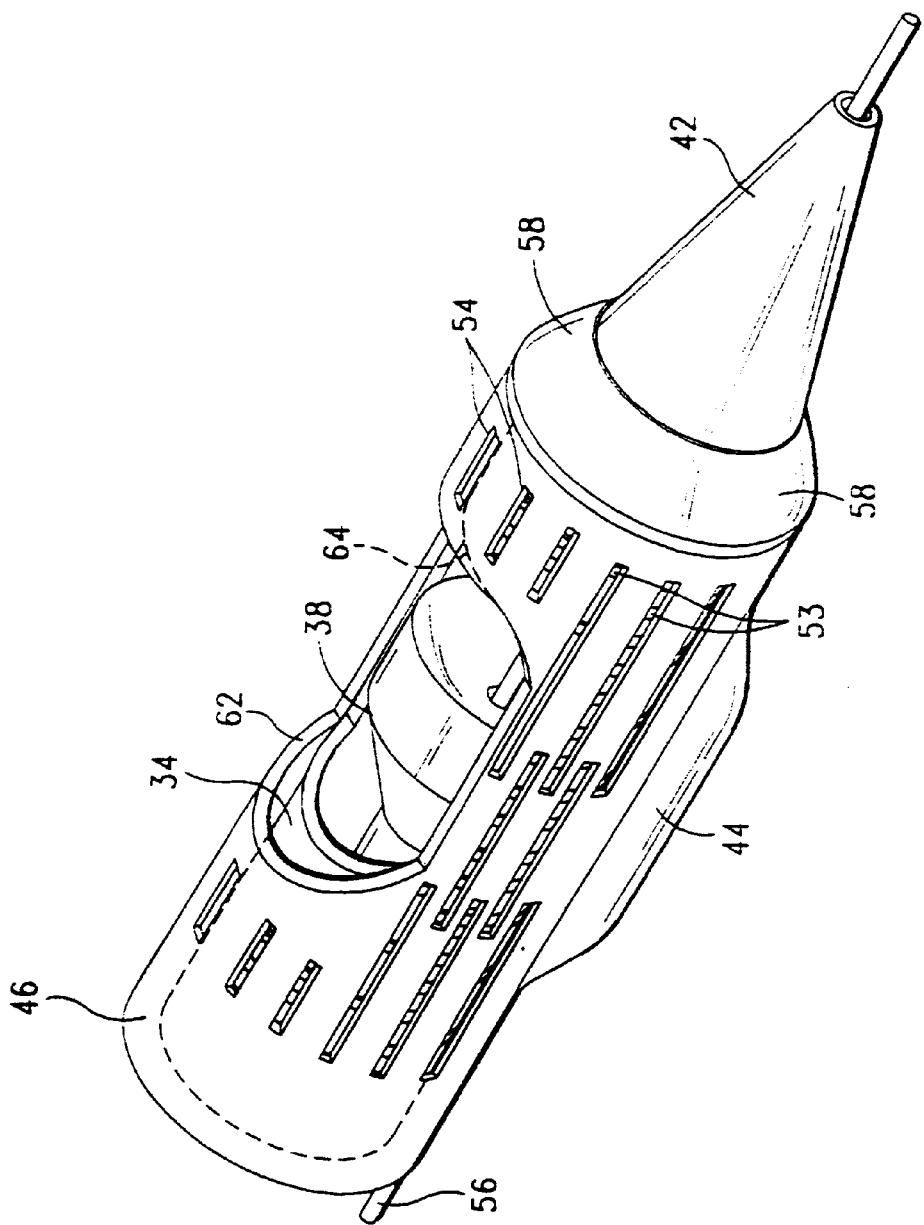
FIG. 4 shows a perspective view of the housing of FIG. 2 with a sleeve over the housing.

With particular reference to FIG. 4, there is shown the sleeve 46. The opening 62 of the sleeve 46 aligns with the opening 64 of the housing 34. The stopper 58 engages one end of the sleeve 46 to hold the sleeve 46 and to prevent the sleeve 46 From sliding over the nosecone 42. The stopper 58 holds the opening 62 in alignment with the opening 64.

The balloon 44 and a balloon inflation lumen 56 are formed integral with the sleeve 46. The balloon inflation lumen 56 aligns within the sleeve 46 for inflating and a deflating the balloon 44. Inflation of the balloon 44 holds the housing 34 in a biological conduit, for example.

The sleeve 46 has a plurality of axially aligned slots 54 that overlie the slots 53 of the housing. The slots 34 are orthogonal to the slots 53. The slots 54 are evenly spaced in parallel having uniform widths and lengths. The slots 54 facilitate generally uniform rigidity of the sleeve 46.

Figure 5:
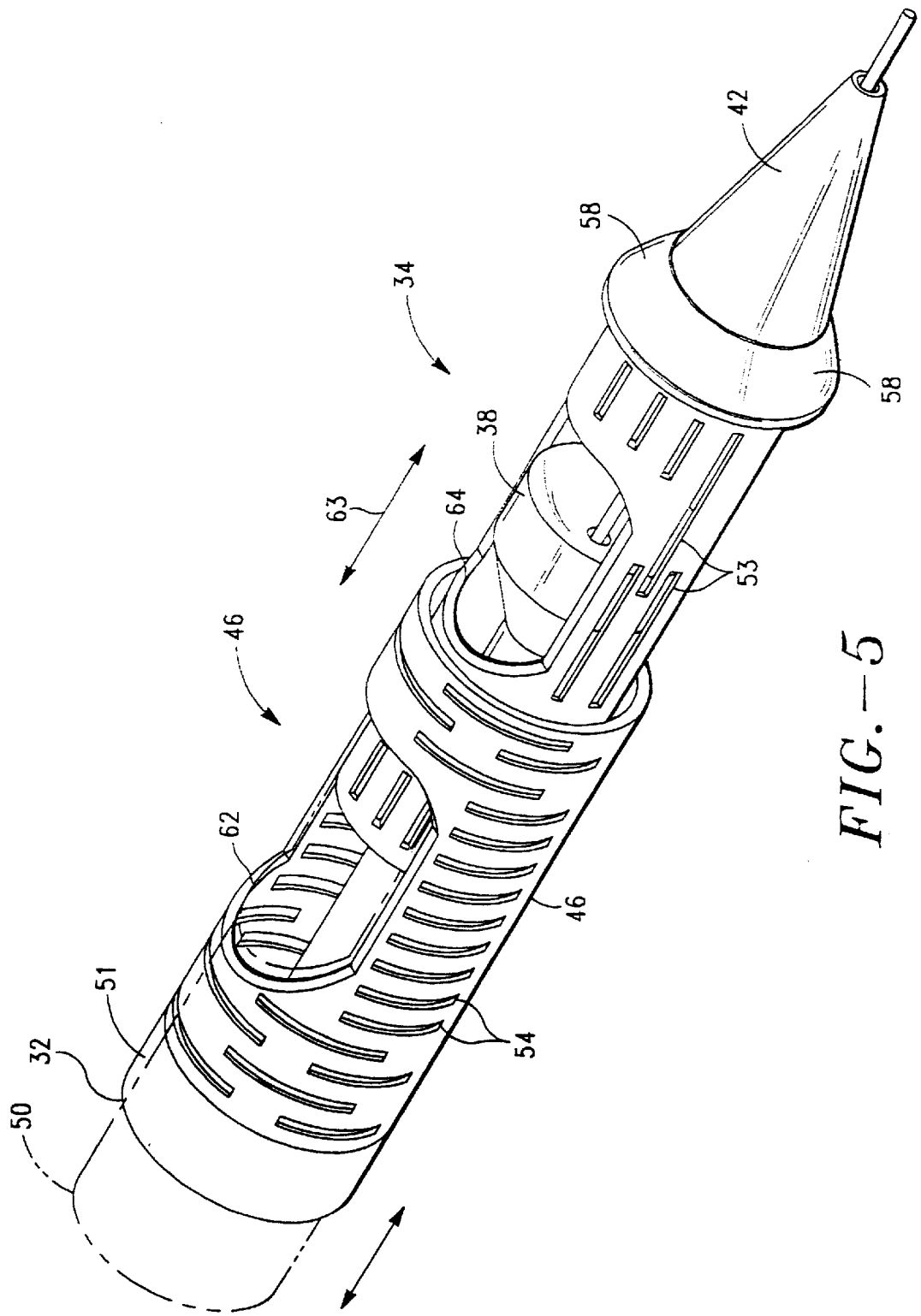
FIG. 5 shows a perspective view of an embodiment of a housing and a sleeve in accordance with the present invention.

With particular reference to FIG. 5, there is shown the housing 34 and the sleeve 46. The housing 34 attaches to the distal end 50 of the catheter body 32. The sleeve 46 is positioned proximal to the housing 34 to facilitate bending of the housing 34. The sleeve 46 slides axially with respect to the housing 34 in the direction of the arrows 63. The catheter body 32 includes a slidable outer sheath 51. The outer sheath 51 attaches to the sleeve 46 to slide and move the sleeve 46 with respect to the housing 34.

The sleeve 46 has a plurality of radially aligned slots 54. The slots 54 of the sleeve 46 are orthogonal to the slots 53 of the housing 34. Relative positioning of the sleeve 46 with respect to the housing 34 orthogonally aligns the slots 53 and 54 to reinforce the housing 34.

It can be appreciated that a sleeve 46 having slots 54 and a housing 34 having slots 53 can be configured so that the slots 53 and 54 have various slot angles. Varied and uniform slot spacing can be employed in accordance with the present invention.

Figure 6:
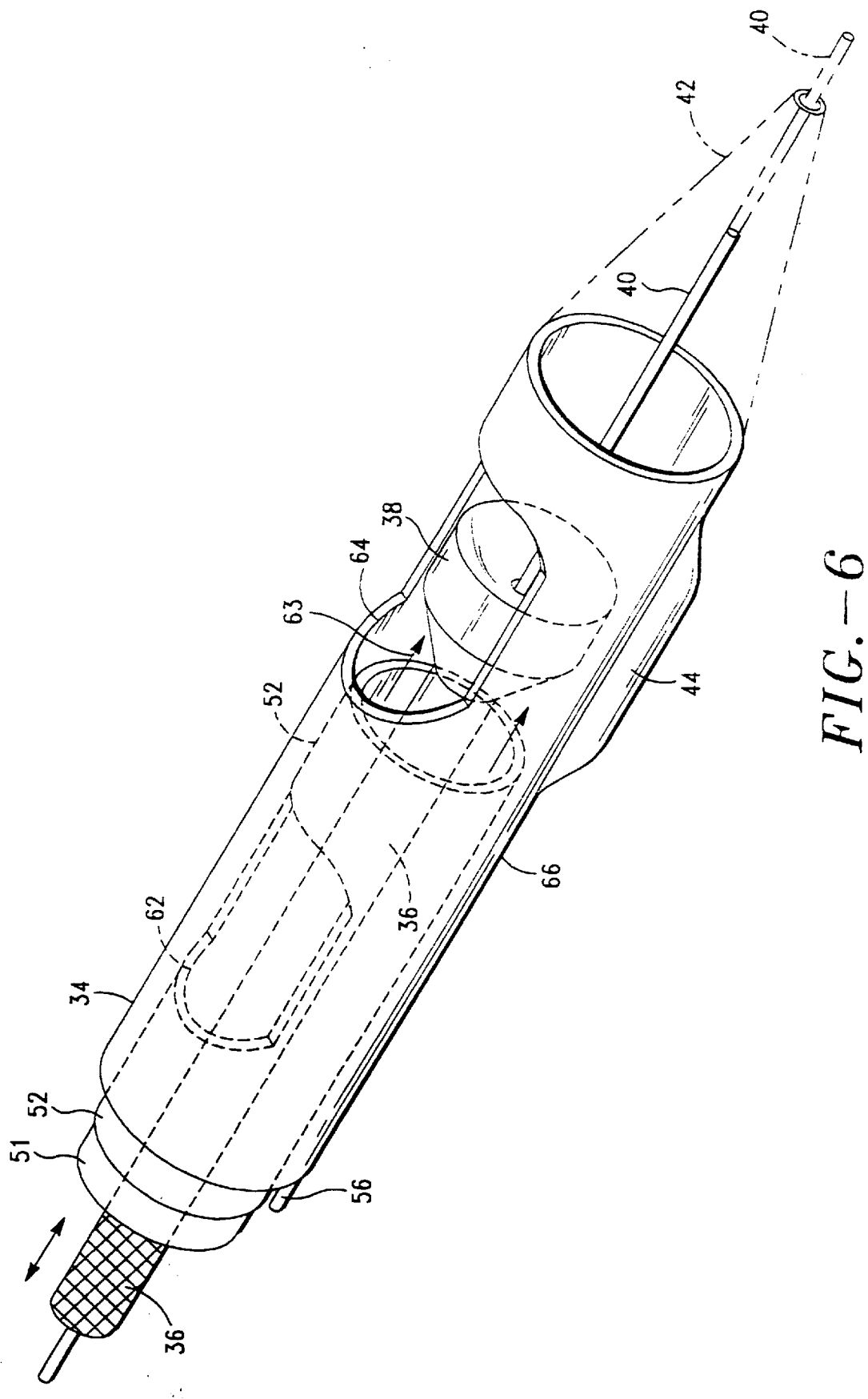
FIG. 6 shows a perspective view of an embodiment of a housing and a sleeve in accordance with the present invention.

With particular reference to FIG. 6, there is generally shown the housing 34 and an internal sleeve 52. The sleeve 52 slidably mounts within the housing 34. The housing 34 surrounds a portion of the sleeve 52. The sleeve 52 surrounds the torque cable 36 and the work element 38 to align the work element in the housing 34. The torque cable 36 translates and rotates the work element 38 with respect to the housing 34 within the sleeve 46. The work element 38, the torque cable 36, and the sleeve 52 move independently within the housing 34 to enable the sleeve to selectively reinforce the housing.

The housing 34 has a lateral side 66. The balloon 44 attaches to the housing 34 on a lateral side of the housing 34. The balloon inflation lumen 56 extends axially alone the lateral side 66 of the housing 34 and communicates with the balloon 44.

The sleeve 52 slides in the direction of the arrows 63 from one position where the housing 34 is distal the sleeve 52, to another position where the opening 62 of the sleeve 52 aligns with the opening 64 of the housing 34. When the openings 62 and 64 align, the sleeve 52 reinforces the housing 34 to inhibit bending of the housing 34 and to enable reliable operation of the work element 38. The sleeve 52 inhibits interference between the work element 38 and the housing 34. The sleeve 52 guides the work element 38 within the housing 34 and inhibits deformation of the opening 64 to inhibit escape of the work element 38 from the housing 34.

The sleeve 52 slides over the work element 38. The opening 62 of the sleeve exposes the work element 38 when the opening 62 of the sleeve 52 aligns with the opening 64 of the housing 34. In this position, the sleeve 52 reinforces the housing 34 to inhibit deformation of the opening 64.

With particular reference to FIG. 7, there is generally shown the housing 34. The slots 53 enable the housing 34 to bend and axially compress. The housing 34 has a distal end 84. A pair of wires 70 slidably mount within the housing 34 and attach to the distal end 84. The wires 70 extend from the distal end 84 of the housing 34 through the catheter body 32 to the proximal end 48 of the catheter body 32 (FIG. 1).

Each wire 70 has an end 78 attached to the housing 34 near the nose cone 42. The wire 70 aligns along the inner wall 71 of the housing 34. Each wire 70 is pulled in the direction of the arrows 73, by an operator, for example. Pulling the wires 70 stretches the wires 70 and applies a compressive force on the housing 34. This compressive force slightly compresses the housing 34 from an original shape and reinforces the housing 34 through increased resistance to bending. The housing 34 springs back to the original shape when the compressive force applied by the wire 70 is eliminated.

The work element 38 has a groove 69. During operation of the work element 38, the wires 70 align with the groove 69 and guide the work element 38 within the housing 34 when the work element 38 reciprocates.

With particular reference to FIG. 8 there is shown a cross section of FIG. 7 as seen along the line 8—8 in the direction of the arrows. The wire 70 has a rectangular cross-section 72. The housing 34 has an inner wall 71. The wire 70 attaches along the inner wall 71. The cross-section 72 is rectangular to guide the work element within the housing 34.

It can be appreciated that the wire 70 may extend along an outer wall or be formed within the housing 34.

With particular reference to FIG. 9, there is shown an embodiment of the housing 34. The wires 70 are normally relaxed to facilitate flexion of the housing 34. When the wires 70 are pulled in the direction of the arrows 73, the wires 70 tense and slide axially in the direction of the arrows 73 to axially compress the housing 34. The wires 70 axially compress the housing 34 in an amount shown as Δ/. The housing 34 becomes more rigid when axially compressed as compared with the uncompressed configuration which is shown in phantom.

With particular reference to FIG. 10, there is shown a cross-section of the housing 34 of FIG. 9 as seen along the line 10—10 in the direction of the arrows. The wire 70 has a circular cross-section. The wire 70 includes a coaxial protective covering 74. The wire 70 is formed from stainless steel. The covering 74 is formed from plastic.

Figure 11:
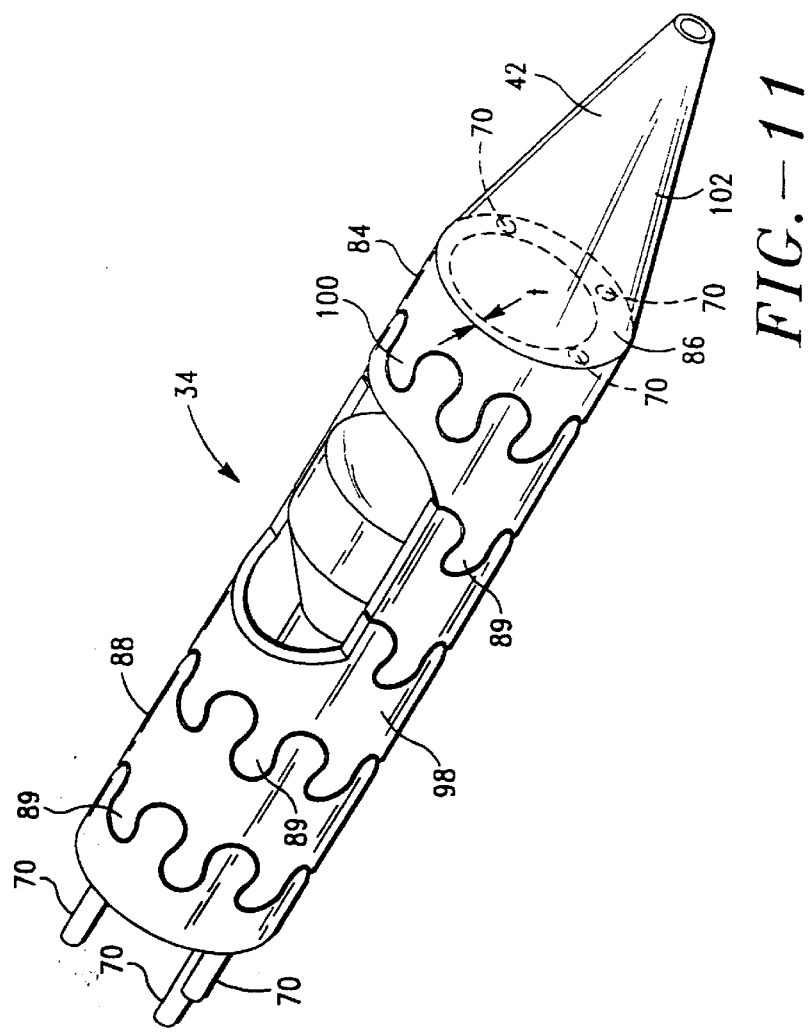
FIG. 11 shows a perspective view of an embodiment of the housing in accordance with the present invention.

With particular reference to FIG. 11, there is shown the housing 34. The housing 34 includes multiple discrete segments 88. Each segment 88 abuts an adjacent segment 88. Abutting segments 88 interlock. Each segment 88 has jigsaw puzzle piece connectors 89 which normally loosely interconnect abutting segments 88 to enable flexion (e.g. bending) of the housing.

The housing 34 includes three wires 70, a wall 86, a top side 100 and a bottom side 102. The wires 70 are interspersed on the bottom side 102 of the housing 34. The wires 70 extend from the distal end 84 of the housing 34, through the housing 34 and through the catheter body 32 (FIG. 1). When the wires 70 are pulled, the wires 70 slide with respect to the housing 34. The housing 34 compresses and the segments 88 tightly interconnect to inhibit bending of the housing 34. The housing 34 has a non-uniform thickness "t". The top side is relatively thin and the bottom side is relatively thick so that when compressed by the wires 70, the housing compresses uniformly. The wires 70 extend through the wall 86 of the housing 34.

It can be appreciated that the cooperation of the wires and the housing 34 is operable in many forms. For example, the housing 34 can have a uniform thickness. Additionally, the wires 70 may mount both internal to and external to the housing 34.

Figure 12:
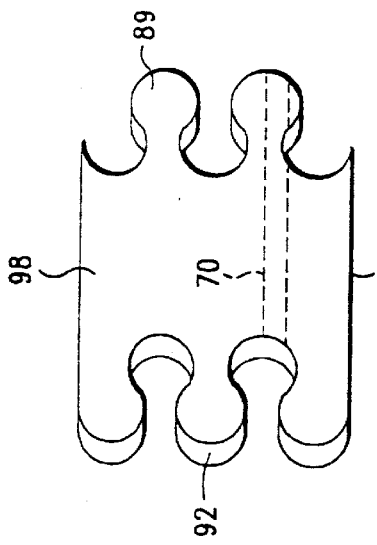
FIG. 12 is a side view of an embodiment of a segment of the housing of FIG. 11.

FIG. 12 shows a segment 88 of the housing 34. The segment 88 has beveled edges 92 and a surface 98. Each beveled edge 92 mates with a beveled edge 92 of an adjacent segment 88 to enable flexion of the housing 34 (FIG. 11) and to ease interconnection of the segments 88.

Figure 13:
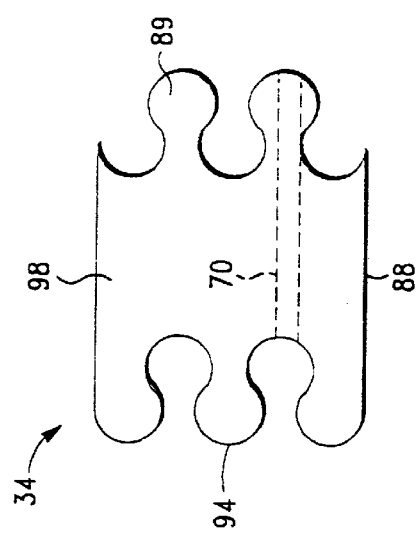
FIG. 13 is a side view of an embodiment of a segment of the housing of FIG. 11.

FIG. 13 shows a segment 88 of the housing 34. The segment 88 has squared edges 94. The squared edges 94 align each segment 88 with an adjacent segment 88.

Various modifications and changes in the invention as described may be made in accordance with the scope of the present invention. For example, the housing 34 may be adapted in a variety of ways to enable the housing 34 to flex. The housing 34 may be fabricated from any of a variety of flexible materials. The sleeve may include any of a variety of mechanical structures which enable the housing 34 to become rigid. The sleeve may be fabricated from a variety of materials including alloys which are designed to spring back into an original shape as desired. The present invention is limited in scope only by the appended claims.

I claim:

1. A catheter device for use in a biological conduit having tortuous regions, comprising:

a catheter body having a proximal end and a distal end;

a housing connected to the distal end of the catheter body, the housing being flexible to facilitate insertion of the catheter device into the tortuous regions of the biological conduit, the housing being capable of guiding a moveable work element, the housing having a number of discrete segments;

a work element movably attached to operate within the housing; and a reinforcing means slidably attached to the housing for selectively reinforcing the housing to facilitate operation of the work element, the reinforcing means including a wire which attaches to the housing and extends along the housing, the wire normally being relaxed to facilitating flexion of the housing, the wire tensing to selectively reinforce the housing, whereby, when the catheter device is inserted in the biological conduit, the reinforcing means reinforces the housing to facilitate operation of the work element.

2. A catheter device for use in a biological conduit having tortuous regions, comprising:

a catheter body having a proximal end and a distal end;

a housing connected to the distal end of the catheter body, the housing being flexible to facilitate insertion of the catheter device into the tortuous regions of the biological conduit, the housing being capable of guiding a moveable work element, the housing being axially compressible to normally facilitate flexion of the housing;

a work element movably attached to operate within the housing; and a reinforcing means slidably attached to the housing for selectively reinforcing the housing to facilitate operation of the work element, the reinforcing means including a wire which is normally relaxed and extends along the housing, the wire sliding and tensing to compress the housing to selectively provide lateral support to the housing, whereby, when the catheter device is inserted in the biological conduit, the reinforcing means reinforces the housing to facilitate operation of the work element.

3. A device as set forth in claim 2, wherein the reinforcing means includes several wires, each wire being aligned in parallel with the axis of the housing.

4. A catheter device for use in a biological conduit having tortuous regions, comprising:

a catheter body having a proximal end and a distal end;

a housing connected to the distal end of the catheter body, the housing being flexible to facilitate insertion of the catheter device into the tortuous regions of the biological conduit, the housing being capable of guiding a moveable work element, the housing being formed with a plurality of slots;

a work element movably attached to operate within the housing; and a reinforcing means slidably attached to the housing for selectively reinforcing the housing to facilitate operation of the work element, wherein the reinforcing means includes a sleeve formed with a plurality of slots, the housing circumscribes a portion of the sleeve, the slots of the sleeve align orthogonal to the slots of the housing to provide lateral support to the housing when the housing circumscribes the sleeve, and the sleeve slides from one position wherein the housing is flexible to another position wherein the sleeve internally supports to the housing, whereby, when the catheter device is inserted in the biological conduit, the reinforcing means reinforces the housing to facilitate operation of the work element.

5. A catheter device for use in a biological conduit having tortuous regions, comprising:

a catheter body having a proximal end and a distal end;

a housing connected to the distal end of the catheter body, the housing being flexible to facilitate insertion of the catheter device into the tortuous regions of the biological conduit, the housing being capable of guiding a moveable work element;

a work element movably attached to operate within the housing; and a reinforcing means slidably attached to the housing for selectively reinforcing the housing to facilitate operation of the work element, the reinforcing means including a wire, the wire extending along the catheter body and the housing, the wire being axially slideable from one position where the wire is relaxed to another position where the wire is tense to provide lateral support to the housing when the wire is tense, whereby, when the catheter device is inserted in the biological conduit, the reinforcing means reinforces the housing to facilitate operation of the work element.

6. A device as set forth in claim 5, wherein the wire is enclosed in a protective covering.

* * * * *